United States Patent
Broghammer et al.

(10) Patent No.: US 10,940,009 B2
(45) Date of Patent: Mar. 9, 2021

(54) JOINT SOCKET AND JOINT ENDOPROSTHESIS

(71) Applicant: Aesculap AG, Tuttlingen (DE)

(72) Inventors: Tanja Broghammer, Dunningen (DE); Joerg Fritzsche, Frittlingen (DE); Jens Schneider, Radolfzell (DE); Kai Bisser, Seitingen-Oberflacht (DE)

(73) Assignee: Aesculap AG, Tuttlingen (DE)

( * ) Notice: Subject to any disclaimer, the term of this patent is extended or adjusted under 35 U.S.C. 154(b) by 35 days.

(21) Appl. No.: 16/260,348

(22) Filed: Jan. 29, 2019

(65) Prior Publication Data
US 2019/0159903 A1 May 30, 2019

Related U.S. Application Data

(63) Continuation of application No. PCT/EP2017/069647, filed on Aug. 3, 2017.

(30) Foreign Application Priority Data

Aug. 3, 2016 (DE) .................... 10 2016 114 368.5

(51) Int. Cl.
*A61F 2/34* (2006.01)
*A61F 2/30* (2006.01)
*A61B 17/86* (2006.01)

(52) U.S. Cl.
CPC ............ *A61F 2/34* (2013.01); *A61F 2/30744* (2013.01); *A61B 17/86* (2013.01); *A61F 2/30771* (2013.01);
(Continued)

(58) Field of Classification Search
CPC ........................... A61F 2/34; A61F 2002/3401
See application file for complete search history.

(56) References Cited

U.S. PATENT DOCUMENTS

| | | |
|---|---|---|
| 5,370,702 A | 12/1994 | Jones |
| 5,571,198 A | 11/1996 | Drucker et al. |

(Continued)

FOREIGN PATENT DOCUMENTS

| | | |
|---|---|---|
| CN | 101600403 | 12/2009 |
| CN | 102596106 | 7/2012 |

(Continued)

OTHER PUBLICATIONS

KKS Ultraschall AG; "Innovation times three"; Swiss Medtech Industry; Edition 2015; pp. 12-19.

*Primary Examiner* — Bruce E Snow
*Assistant Examiner* — Melissa A Hoban
(74) *Attorney, Agent, or Firm* — Lipsitz & McAllister, LLC (57) ABSTRACT

The invention relates to a joint socket for a joint endoprosthesis, in particular in the form of a hip joint socket for a hip joint endoprosthesis. The joint socket has the form or substantially the form of a section of a hollow-spherical shell. The joint socket comprises a socket wall, in which socket wall at least one through-opening is formed. The through-opening is closed with a closure element. The closure element is formed as one piece with the socket wall. At least one predetermined breaking point is formed between the closure element and the socket wall. The at least one predetermined breaking point is irreversibly destroyable for removing the closure element from the socket wall. The joint socket comprises at least one connecting device for force- and/or form-fittingly connecting the closure element removed from the socket wall to the socket wall in a connecting position.

28 Claims, 7 Drawing Sheets

(52) U.S. Cl.
CPC .......... *A61F 2002/305* (2013.01); *A61F 2002/30331* (2013.01); *A61F 2002/30561* (2013.01); *A61F 2002/3401* (2013.01); *A61F 2310/00011* (2013.01); *A61F 2310/00023* (2013.01); *A61F 2310/00407* (2013.01)

(56) References Cited

U.S. PATENT DOCUMENTS

| | | | |
|---|---|---|---|
| 5,782,929 | A | 7/1998 | Sederholm |
| 8,764,843 | B2 | 7/2014 | Gradel |
| 8,845,748 | B2 | 9/2014 | Gradel |
| 8,882,849 | B2 | 11/2014 | Gradel |
| 9,168,143 | B2 | 10/2015 | Gradel |
| 10,588,751 | B2 * | 3/2020 | Macke ............ A61F 2/30744 |
| 2003/0135281 | A1 * | 7/2003 | Hanssen ............ A61F 2/34 623/22.35 |
| 2010/0063597 | A1 | 3/2010 | Gradel |
| 2010/0306987 | A1 | 12/2010 | Gradel |
| 2012/0197412 | A1 | 8/2012 | Gradel |
| 2013/0041474 | A1 | 2/2013 | Davenport et al. |
| 2013/0310945 | A1 | 11/2013 | Slone et al. |
| 2014/0364958 | A1 | 12/2014 | Gradel |
| 2017/0333192 | A1 | 11/2017 | Zhou et al. |

FOREIGN PATENT DOCUMENTS

| | | |
|---|---|---|
| CN | 205322552 | 6/2016 |
| CN | 105748174 | 7/2016 |
| DE | 69406786 | 3/1998 |
| DE | 102005028523 | 11/2006 |
| EP | 0341199 | 11/1989 |
| EP | 0701420 | 11/1997 |
| EP | 1163891 | 12/2001 |
| EP | 1338256 | 8/2003 |
| FR | 2826865 | 1/2003 |
| WO | 9515734 | 6/1995 |

\* cited by examiner

JOINT SOCKET AND JOINT ENDOPROSTHESIS

CROSS-REFERENCE TO RELATED APPLICATIONS

This application is a continuation of international application number PCT/EP2017/069647 filed on Aug. 3, 2017 and claims the benefit of German application number 10 2016 114 368.5 filed on Aug. 3, 2016, which are incorporated herein by reference in their entirety and for all purposes.

FIELD OF THE INVENTION

The present invention relates to joint sockets for joint endoprostheses generally, and more specifically to a joint socket for a joint endoprosthesis, in particular in the form of a hip joint socket for a hip joint endoprosthesis, which joint socket has the form or substantially the form of a section of a hollow-spherical shell, wherein the joint socket comprises a socket wall, in which socket wall at least one through-opening is formed, which through-opening is closed with a closure element, which closure element is formed as one piece with the socket wall, wherein at least one predetermined breaking point is formed between the closure element and the socket wall, which at least one predetermined breaking point is irreversibly destroyable for removing the closure element from the socket wall.

Further, the present invention relates to joint endoprostheses generally, and more specifically to a joint endoprosthesis, in particular in the form of a hip joint endoprosthesis, comprising a joint socket and a shank, in particular in the form of a femur shank, which is coupled to the joint socket in a ball-jointed manner.

BACKGROUND OF THE INVENTION

Joint sockets and joint endoprostheses of the kind described at the outset are known in a variety of ways, for example disclosed by DE 694 06 786 T2.

Joint sockets of that kind enable a surgeon to, as required, irreversibly separate one or more closure elements out of the socket wall in order to expose the through-opening which is closed or substantially closed by the respective closure element after the production of the joint socket. In particular a fixing screw may then be guided through the exposed through-opening in order to fix the joint socket to the bone.

The separating out of one or more closure elements typically takes place during the implantation of the joint endoprosthesis. Thus only those through-openings which are actually required are exposed by detaching the closure elements.

One problem with joint sockets of the kind described at the outset is re-closing a through-opening if it is ultimately indeed not required for screwing a bone screw through the socket wall into the bone in order to fix the joint socket to the bone.

SUMMARY OF THE INVENTION

In a first aspect of the invention, a joint socket for a joint endoprosthesis, in particular in the form of a hip joint socket for a hip joint endoprosthesis, is provide which joint socket has the form or substantially the form of a section of a hollow-spherical shell. The joint socket comprises a socket wall, in which socket wall at least one through-opening is formed. The through-opening is closed with a closure element. The closure element is formed as one piece with the socket wall. At least one predetermined breaking point is formed between the closure element and the socket wall. The at least one predetermined breaking point is irreversibly destroyable for removing the closure element from the socket wall. The joint socket comprises at least one connecting device for force- and/or form-fittingly connecting the closure element removed from the socket wall to the socket wall in a connecting position.

In a second aspect of the invention, a joint endoprosthesis is provided, in particular in the form of a hip joint endoprosthesis. The joint endoprosthesis comprises a joint socket and a shank, in particular in the form of a femur shank. The shank is coupled to the joint socket in a ball-jointed manner. The joint socket is configured in the form of a joint socket having the form or substantially the form of a section of a hollow-spherical shell. The joint socket comprises a socket wall, in which socket wall at least one through-opening is formed. The through-opening is closed with a closure element. The closure element is formed as one piece with the socket wall. At least one predetermined breaking point is formed between the closure element and the socket wall. The at least one predetermined breaking point is irreversibly destroyable for removing the closure element from the socket wall. The joint socket comprises at least one connecting device for force- and/or form-fittingly connecting the closure element removed from the socket wall to the socket wall in a connecting position.

BRIEF DESCRIPTION OF THE DRAWING FIGURES

The foregoing summary and the following description may be better understood in conjunction with the drawing figures, of which.

DETAILED DESCRIPTION OF THE INVENTION

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a joint socket for a joint endoprosthesis, in particular in the form of a hip joint socket for a hip joint endoprosthesis, which joint socket has the form or substantially the form of a section of a hollow-spherical shell, wherein the joint socket comprises a socket wall, in which socket wall at least one through-opening is formed, which through-opening is closed with a closure element, which closure element is formed as one piece with the socket wall, wherein at least one predetermined breaking point is formed between the closure element and the socket wall, which at least one predetermined breaking point is irreversibly destroyable for removing the closure element from the socket wall, wherein the joint socket comprises at least one connecting device for force- and/or form-fittingly connecting the closure element removed from the socket wall to the socket wall in a connecting position.

The proposed further development of a known joint socket thus enables in particular reconnecting the closure element to the socket wall in a defined manner, in particular in a force- and/or form-fitting manner. This enables a surgeon to re-close the through-opening with the closure element as required. In particular, no further closure elements are required for this purpose. Those closure elements may be used which are first connected to the socket wall by way of the at least one predetermined breaking point after the production of the joint socket. It is thus in particular ensured that the necessary number of closure elements are always available for the implantation of the joint socket. As the case may be, even all exposed through-openings may be re-closed with the closure elements provided for this purpose. In particular, multiple through-openings are provided which are each closed with a closure element. In particular, the through-openings and the closure elements may be of identical configuration, so that a closure element which has been separated out may not only be used for closing that through-opening which was initially closed with said closure element, but also may be used for closing any other through-opening.

The joint socket favorably has a spherical or substantially spherical outer surface and a hollow-spherical or substantially hollow-spherical inner surface. Thus, for one, a bone may be prepared for the insertion of the joint socket in a simple manner with a spherical milling cutter. For another, for example, a joint head of a joint shank may be inserted directly into the joint socket or a corresponding insert for forming an optimal sliding pairing in connection with the joint head of the joint shank.

It is favorable if the at least one connecting device is configured in the form of a screw connecting device, a bayonet connecting device, a turning clamp connecting device, or a snapping connecting device. The stated connection types enable in particular a quick and secure connection of the closure element to the socket wall. A connection may in particular be produced in a defined manner in order to prevent an unintended detachment of the closure element from the through-opening in the socket wall.

It is advantageous if the at least one connecting device comprises at least one first connecting element and at least one second connecting element, if the at least one first connecting element is arranged or formed on the socket wall, and if the at least one second connecting element is arranged or formed on the at least one closure element. Thus, one, two, three, four, or more first connecting elements or also, correspondingly, one, two, three, four, or more second connecting elements may be provided which, not necessarily in a corresponding number, are in engagement with each other in the connecting position. In particular, the at least one first connecting element is arranged or formed on the socket wall on or in the region of the through-opening. The joint socket may thus additionally be formed to be particularly compact.

It is favorable if the at least one first connecting element and the at least one second connecting element in the connecting position are in engagement in a force- and/or form-fitting manner and in a separating position, in which the at least one predetermined breaking point is irreversibly destroyed and the closure element unblocks the at least one through-opening, are disengaged. The closure element initially closing the at least one through-opening may thus be entirely separated from the joint socket and handled and, as required, be reused for closing the at least one through-opening.

In a simple manner, the closure element may be screwed into the socket wall for closing a through-opening if the at least one first or second connecting element comprises an internal or external thread section. For example, the at least one first connecting element may comprise an internal thread section and the at least one second connecting element a corresponding external thread section or vice versa.

Further, it may be advantageous if the at least one first or second connecting element is configured in the form of a projection or in the form of a recess corresponding to the projection. For example, the at least one first connecting element may thus be configured in the form of a projection and the at least one second connecting element in the form of a corresponding recess or vice versa. For example, two, three, or more protections and associated recesses may be provided, in particular for forming a bayonet connection.

The at least one through-opening favorably defines a longitudinal axis which runs in radial direction or substantially in radial direction in relation to a center of the shell. This enables in particular inserting fixing screws in radial direction for fixing the joint socket to a bone, likewise in radial direction in relation to the center of the shell. In this way, heads of the bone screws only minimally project from the socket wall in the direction to the center, or even not at all.

This facilitates, as the case may be, the insertion and connection of a joint insert into and to the joint socket.

For forming a bayonet connection or a turning clamp connection, it is in particular favorable if the projection is arranged or formed protruding from the at least one closure element in radial direction in relation to the longitudinal axis or projecting in the direction toward the longitudinal axis from a rim of the socket wall delimiting the through-opening. The at least one closure element may thus be transferred, e.g., from the separating position into the connecting position by rotating about the longitudinal axis if a projection formed on the closure element is brought into engagement with the corresponding recess formed on the rim of the through-opening upon the rotational movement.

It is advantageous if the recess corresponding to the projection is arranged or formed in a rim of the socket wall, which rim delimits the through-opening, so as to be open facing in the direction toward the longitudinal axis or open facing from the at least one closure element in radial direction in relation to the longitudinal axis. A recess formed in that way may in particular be brought into engagement with a projection which is formed protruding from the closure element or from the socket wall facing in the opposite direction. In particular, a bayonet or turning clamp connection may thus be formed in a simple manner.

The recess preferably comprises at least one groove section which is open facing in the direction toward the longitudinal axis or in radial direction away from the longitudinal axis. A corresponding projection may thus easily and securely be guided in the recess and, as the case may be, clamped therein, for example if the connecting device is configured in the form of a bayonet or turning clamp connection.

Further, it may be advantageous if the recess is open at least in sections facing in the direction toward a center of the shell for forming an insertion opening for the projection or at least a part thereof in an insertion direction running parallel or substantially parallel to the longitudinal axis. This configuration enables in particular inserting the closure element into the through-opening in parallel to the insertion direction and then rotating the closure element relative to the through-opening when the projection is already in contact with the recess, wherein the projection and the recess come into engagement with each other in a force- and/or form-fitting manner in order to securely and permanently fix the closure element in the through-opening.

The internal or external thread section is favorably arranged or formed on the projection. Thus, multiple mutually separate but overall cooperating internal or external thread sections may be provided which are each arranged or formed on a projection.

It is favorable if, when the predetermined breaking point is undamaged, the projection is arranged in a neutral position of the at least one connecting device in which the projection is arranged in the insertion opening or in the region of the insertion opening. This means in particular that the closure element would not be in engagement with the socket wall in a force- and/or form fitting manner if the predetermined breaking point were severed. This enables in particular detaching closure elements, which have not been separated out, from the socket wall by breaking the at least one predetermined breaking point, but then immediately transferring said closure elements from the neutral position, which the closure elements then adopt, into the connecting position, for example by screwing or rotating into the and relative to the socket wall, respectively.

The closure element in the neutral position with the predetermined breaking point irreversibly destroyed is favorably in engagement with the socket wall neither in a force-nor form-fitting manner. This configuration enables in particular simply and easily breaking out the closure element, as only the predetermined breaking point must be destroyed, but a force- and/or form-fitting connection between the closure element and the socket wall does not need to be released.

The at least one predetermined breaking point advantageously has a wall thickness which is significantly smaller than a thickness of the socket wall. The closure element may thus be separated out from the socket wall in a targeted and simple manner. Preferably only the predetermined breaking point is irreversibly destroyed as a result, but the socket wall is not damaged.

It is advantageous if the wall thickness is less than 0.2 times the thickness. It is preferably less than 0.1 times the thickness. The closure element may thus be simply and quickly detached from the socket wall.

Further, it is advantageous if formed in the socket wall is at least one channel which at least partially passes through the socket wall and has a first open end and a second open end, and if the first open end is arranged or formed in the region of the first or second connecting element, and if the second open end passes through the outer surface or the inner surface of the socket wall. Such a configuration of the socket wall with at least one channel enables forming, in a simple manner, the joint socket as one piece, in particular monolithically, from a pulverulent starting material by sintering, for example laser sintering. Providing the at least one channel enables in particular simply and securely removing excess starting material which remains after sintering, e.g., in the region between the at least one first and the at least one second connecting element. The at least one channel may therefore also optionally be referred to as a powder channel. Thus, even partially interengaging structures of the at least one first and the at least one second connecting element, in particular with multiple undercuts, may be produced with each other, e.g., in one single manufacturing step, but without the risk that the powder partially remains in the socket wall and is only able to come out in the course of an implantation of the joint socket. As a result of the second open end passing through the outer surface or the inner surface of the socket wall, an opening of the at least one channel is formed which in particular enables pulverulent starting material to fall out through the inner surface or through the outer surface of the socket wall.

In order to be able to simply and securely remove pulverulent starting material remaining in the region between the at least one first and the at least one second connecting element, it is favorable if a diameter of the at least one channel corresponds to at least about 5 times, in particular 10 times the average diameter of the powder particles from which the joint socket is formed by generative manufacturing process. The diameter of the at least one channel is preferably at least about five times larger than the largest diameter of the powder particles from which the joint socket is formed by a generative manufacturing process. It may thus be assured that the pulverulent starting material for forming the joint socket does not clog the at least one channel and is able to exit the same in a desired manner.

In order to remove starting material which has not solidified from a region between the at least one first and the at least one second connecting element as efficiently as possible, it is advantageous if the joint socket comprises a multitude of channels. For example, one, two, or three channels may be associated with each pairing of a first and a second connecting element in the described manner.

It is further advantageous if the at least one closure element separated out of the socket wall by destroying the at least one predetermined breaking point is transferable from the separating position into the connecting position by screwing in about a longitudinal axis defined by the through-opening or a rotating-in movement about the longitudinal axis. A joint socket which provides a connection of that kind of the at least one closure element to the socket wall for closing the at least one through-opening enables in particular destroying the predetermined breaking point and directly thereafter bringing the closure element into the connecting position, for example by rotating in or screwing in.

In order to further improve the handling of the joint socket, it is favorable if the at least one closure element comprises at least one tool element receptacle. The at least one tool element receptacle may in particular serve to be brought into engagement with a breakaway tool and a connecting tool, respectively, in order to detach the at least one closure element from the socket wall by destroying the at least one predetermined breaking point and, as the case may be, again bringing said closure element into engagement with the socket wall in order to close the at least one through-opening. The at least one tool element receptacle may in particular be configured in the form of a recess or in the form of a projection. For example, it may be configured in the form of a recess with a polygonal cross section or in the form of an internal multi-round.

The at least one tool element receptacle is favorably open in the direction toward the center of the shell. Thus, in particular, a closure element may still be brought into engagement with the joint socket for closing the at least one through-opening when the joint socket is already fixed to the bone. Unneeded through-openings may thus still be closed in a simple manner after the implantation, as the tool element receptacle in the intended implantation is open facing away from the bone and is accessible for a corresponding tool.

It is particularly advantageous for the handling of the joint socket if it is formed as one piece. In particular, it may be formed monolithically. It is thus in particular possible to form the joint socket without parts arranged moveably thereon. In addition, it may thus be assured that the at least one closure element cannot detach from the joint socket in an undesired manner.

It is advantageous if the joint socket is formed by a generative manufacturing process. Thus, practically any undercuts and interengaging elements of the joint socket may be formed without great difficulties. Thus, as a result, in particular complex formations in the region of cooperating first and second connecting elements are possible.

The joint socket is preferably formed by a powder bed process, by a free-forming process, by a liquid material process, or by a different layer structure process. Thus, in particular joint sockets may be made of a metal or a metal mixture or of a plastic or a plastic mixture.

The joint socket may be produced in a simple manner if it is formed by selective laser melting, by selective laser sintering, by selective heat sintering, by solidifying powder material by means of binder, by electron beam melting, by deposit welding, by a metal powder deposition process, by cold gas spraying, by stereolithography, by a process using digital light processing for illumination, by lamination by layers, by 3D screen printing of metals, or by light-controlled electrophoretic deposition. Depending on a material desired for the production of the joint socket, the individually most advantageous manufacturing process may thus be selected for the respective type of joint socket, in order to obtain an optimal stability and rigidity of the joint socket.

The joint socket is favorably made of a metal and/or of a plastic and/or of a metal-plastic mixture. In particular, through a generative manufacturing process, metal-plastic mixtures may be used for forming, e.g., the socket wall. It is also conceivable to make individual regions of the joint socket, on the one hand, of a metal or a metal mixture and, on the other hand, of a plastic or a plastic mixture.

The metal preferably is or contains titanium. Thus, in particular very biocompatible joint sockets may be formed.

Further, it may be advantageous if the plastic is or contains polyetheretherketone. The latter has, in particular, a high biocompatibility.

Further, the invention relates to a joint endoprosthesis, in particular in the form of a hip joint endoprosthesis, comprising a joint socket and a shank, in particular in the form of a femur shank, which is coupled to the joint socket in a ball-jointed manner, wherein the joint socket is configured in the form of a joint socket having the form or substantially the form of a section of a hollow-spherical shell, wherein the joint socket comprises a socket wall, in which socket wall at least one through-opening is formed, which through-opening is closed with a closure element, which closure element is formed as one piece with the socket wall, wherein at least one predetermined breaking point is formed between the closure element and the socket wall, which at least one predetermined breaking point is irreversibly destroyable for removing the closure element from the socket wall, wherein the joint socket comprises at least one connecting device for force- and/or form-fittingly connecting the closure element removed from the socket wall to the socket wall in a connecting position.

The joint endoprosthesis then also has the advantages described above in conjunction with preferred embodiments of joint sockets. The joint endoprosthesis may optionally also be configured in the form of a shoulder joint endoprosthesis or an intervertebral implant.

It is advantageous if the shank comprises a ball-shaped or substantially ball-shaped joint head, and if the joint socket comprises a joint insert with a joint head receptacle corresponding to the joint head. In this way, an optimized ball joint may be formed with a sliding pairing which has as little wear as possible.

Figure 3:
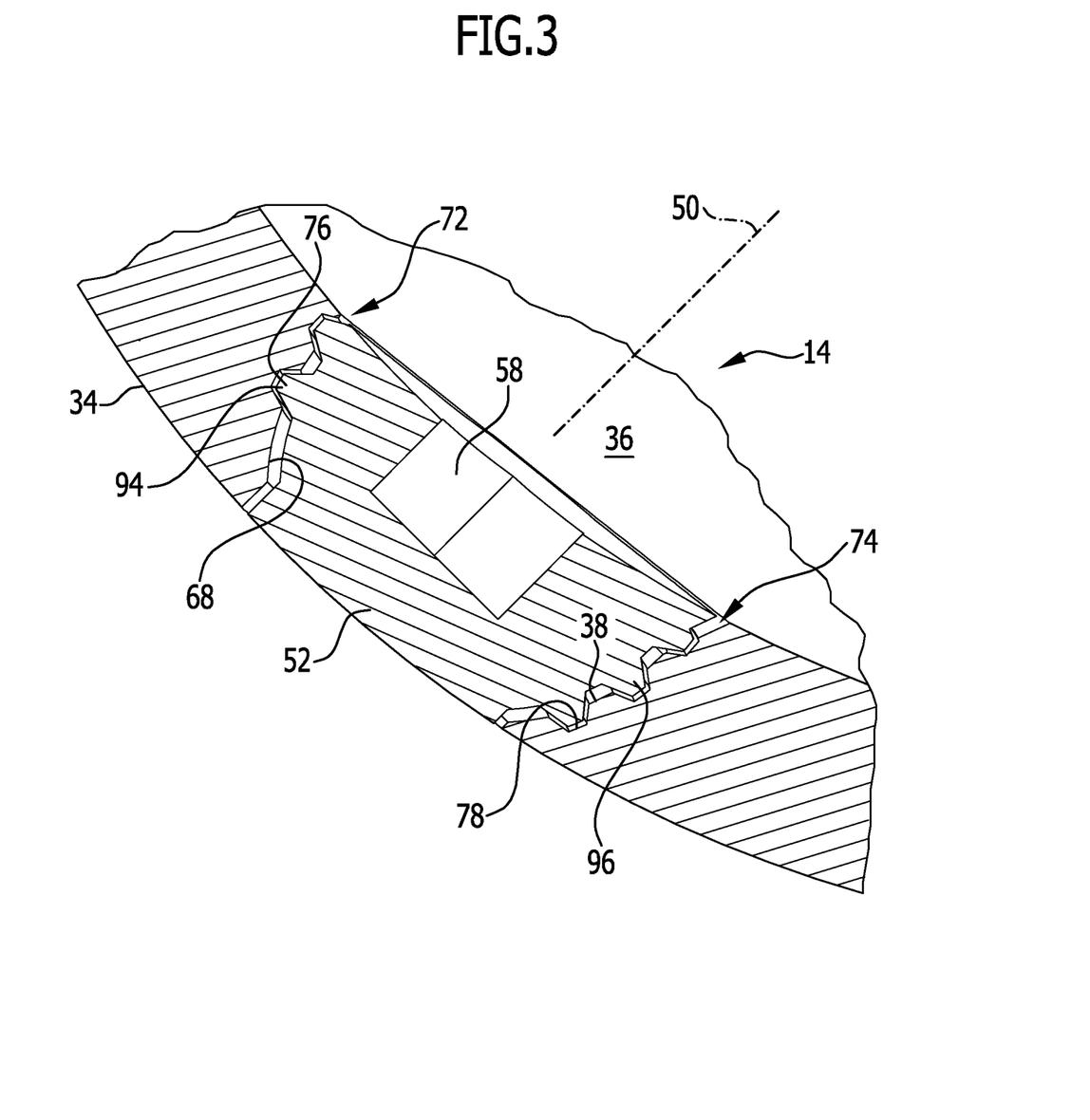
FIG. 3: shows a sectional view similar to FIG. 2B of a further embodiment of a joint socket.
Figure 3A:
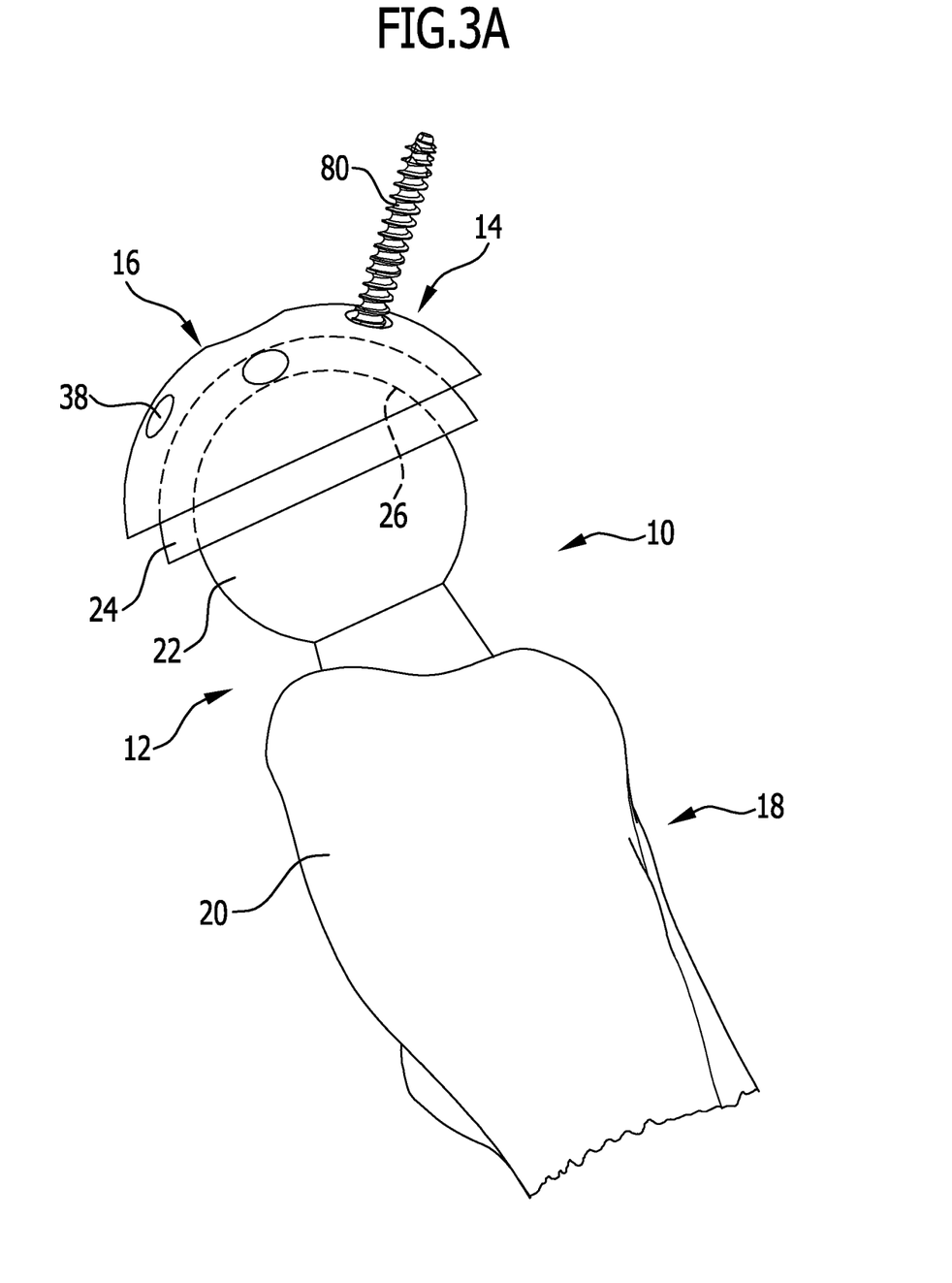
FIG. 3A: shows a schematic partial view of a joint endoprosthesis.

A joint endoprosthesis 10 in the form of a hip joint endoprosthesis 12 is schematically depicted in FIG. 3A.

The joint endoprosthesis 10 comprises a joint socket 14 in the form of a hip joint socket 16 and a shank 18 in the form of a femur shank 20 which is coupled to the joint socket 14 in a ball-jointed manner.

The shank 18 comprises a ball-shaped or substantially ball-shaped joint head 22 which forms a sliding pairing with a joint insert 24 inserted into the joint socket 14. The joint insert 24 has a joint head receptacle 26 corresponding to the joint head 22 for accommodating the joint head 22.

Figure 1A:
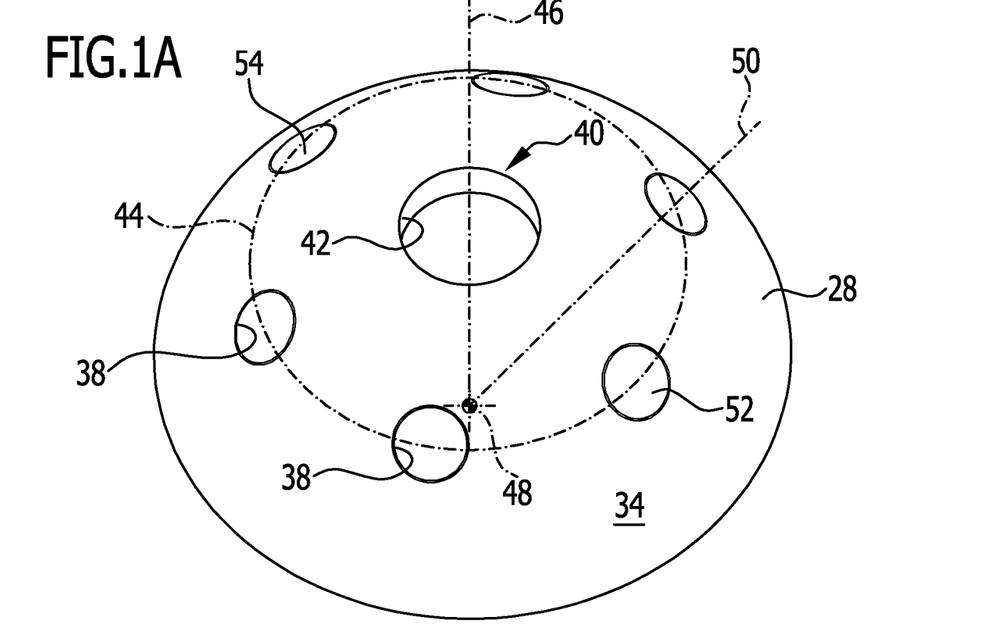
FIG. 1A: shows a perspective view of a joint socket from the outside.
Figure 1B:
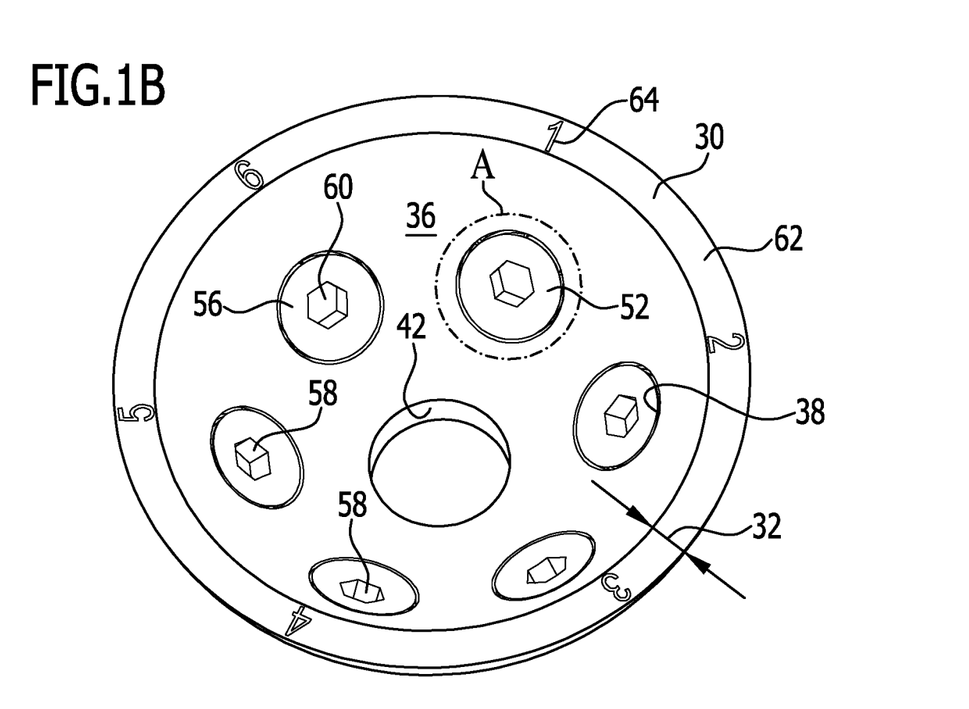
FIG. 1B: shows a perspective view of the joint socket from FIG. 1 from the inside.

The joint socket 14 is depicted in more detail in FIGS. 1A and 1B.

The joint socket 14 is configured in the form or substantially in the form of a section of a hollow-spherical shell 28. The shell 28 comprises a socket wall 30 with a thickness 32 and defines a spherical outer surface 34 and a hollow-spherical or substantially hollow-spherical inner surface 36. In particular, the shell 28 may have the form of a half hollow sphere.

Formed in the socket wall 30 are multiple through-openings 38 which are arranged surrounding a central opening 42 formed in an apex region 40 of the shell 28, namely uniformly on a circle 44 which concentrically surrounds a rotational axis 46. The rotational axis 46 forms an axis of symmetry of the shell 28 in relation to which the shell 28 is formed rotationally symmetrical.

The through-openings 38 are arranged uniformly distributed about the circumference of the circle 44. The through-openings 38 are open facing in radial direction commencing from a center 48 of the joint socket 44 and each define a longitudinal axis 50, such that all longitudinal axes 50 intersect with the rotational axis 46 in the center 48.

In the embodiment of the joint socket 14 schematically depicted in FIGS. 1A and 1B, a total of six through-openings 38 are provided which are each closed with a closure element 52.

The closure elements 52 are formed as one piece with the socket wall 30. An outer surface 54 of the closure element 52, which faces away from the center 48, may in particular have a curvature which corresponds to a curvature of the outer surface 34, so that the outer surface 54 forms, as it were, a part of the outer surface 34.

An inner surface 56 of the closure element 52, which faces in the direction toward the center 48, forms a part of the inner surface 36 in a similar manner.

The closure element 52 further has a tool element receptacle 58 which is open facing in the direction toward the center 48 of the shell 28. The tool element receptacle 58 is configured for example in FIG. 1B as a hexagonal socket 60. Alternatively, other polygonal internal cross section are possible or, e.g., an internal multi-round.

The central opening 42 in the apex region is not closed. It serves in particular for coupling the joint socket 14 to the joint insert 24.

Further, in FIG. 1B, provided on a rim 62 connecting the inner surface 36 to the outer surface 34 is a numbering 64 according to which the six through-openings 38 are numbered clockwise from 1 through 6 in the view depicted in FIG. 1B.

The joint socket 14 is formed as one piece, in particular monolithically. This means that the closure elements 52 are formed as one piece with the shell 28.

Figure 2A:
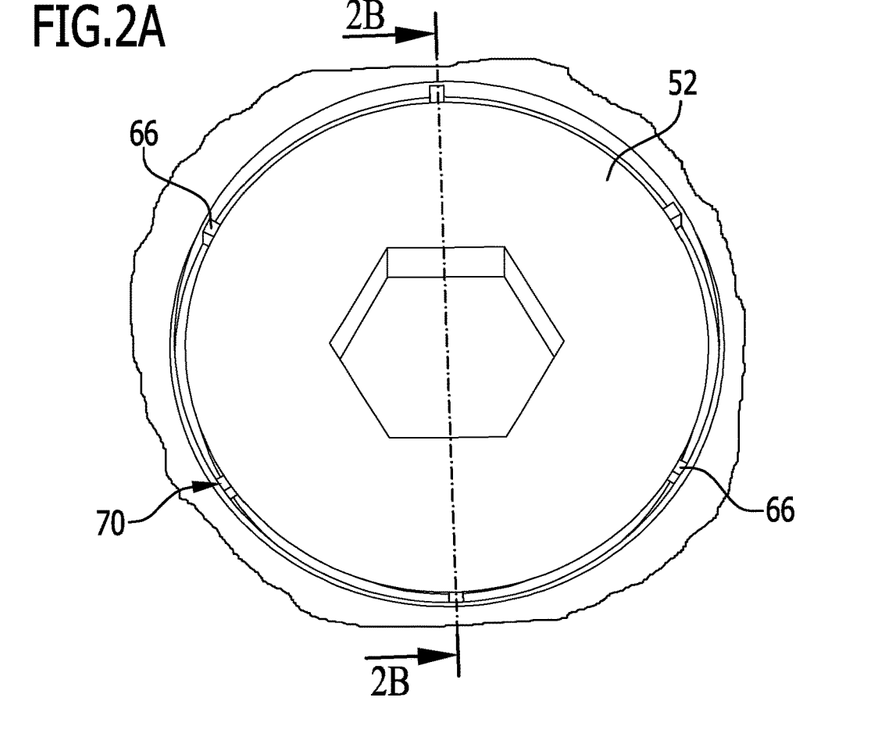
FIG. 2A: shows a schematic, enlarged perspective view of the region A in FIG. 1B.
Figure 2B:
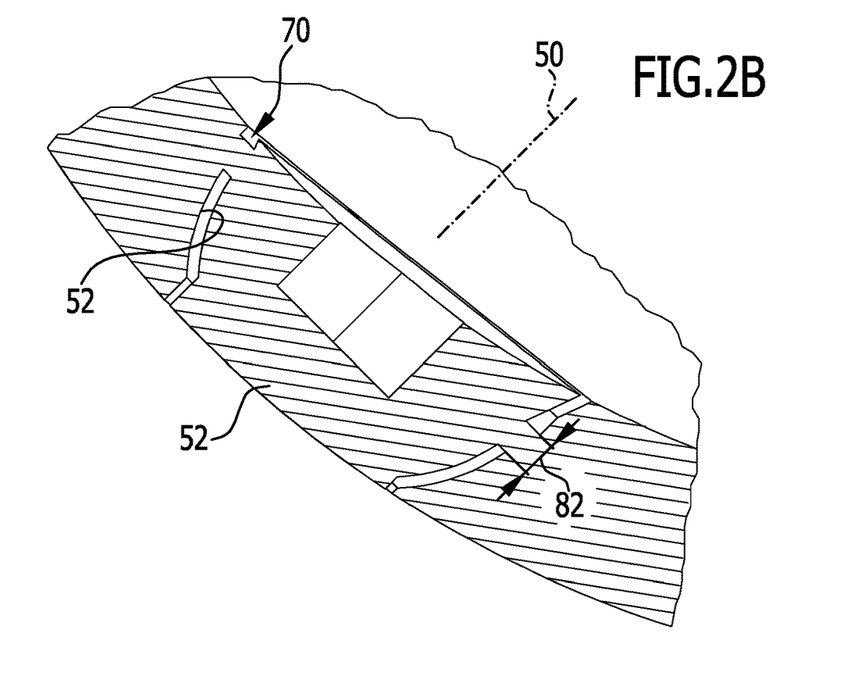
FIG. 2B: shows a sectional view along line 2B-2B in FIG. 2A.

As is depicted for example in FIG. 2A, the closure element 52 is connected, by way of six webs 66 running in radial direction in relation to the longitudinal axis, to a rim 68 facing in the direction toward the longitudinal axis 50 and surrounding the same.

The webs 66 form predetermined breaking points 70 which may be irreversibly destroyed, for example by breaking, in order to detach the closure element 52, which is formed with the shell 28 as one piece, out of the through-opening 38. This may be achieved, for example, by a tool corresponding to the tool element receptacle 58 engaging into the latter and rotating and/or tilting the closure element 52 about the longitudinal axis 50.

A further embodiment of a joint socket 14 is schematically depicted in FIG. 3. For the sake of clarity, identical or similar elements are designated with the same reference numerals. This also applies correspondingly to further, subsequently described embodiments of joint sockets 14.

The closure element 52 may likewise be separated out of the socket wall 30 by way of predetermined breaking points 70 not depicted in FIG. 3.

However, the closure element 52 makes it possible to again be connected to the socket wall 30 in a force- and/or form-fitting manner. A connecting device 72 in the form of a screw connecting device 74 serves for this purpose. After detaching the closure element 52 as described above by engaging a screwing tool into the tool element receptacle 58 and rotating the closure element 52 relative to the socket wall 30, the closure element 52 may be reinserted into the through-opening 38 socket wall 30 and connected thereto in a force- and/or form-fitting manner by a screwing-in movement about the longitudinal axis 50. For this purpose, formed on the closure element 52 is an external thread section 76 with one to three threads and, in the rim 68 in the region of the through-opening 38, an internal thread section 78 also with about one to three threads, namely corresponding to the external thread section 76.

The closure elements 52 may in particular be removed in order to unblock the through-openings 38, through which a fixing element 80 may partially be guided, for example a shank of a bone screw, in order to anchor the joint socket 14 in a bone of a patient.

In case more through-openings 38 were exposed in the implantation of the joint socket 14 by removing the closure elements 52, the latter may again be transferred from a separating position, in which the at least one predetermined breaking point 70 is irreversibly destroyed and the closure element 52 unblocks the respective through-opening 38, into a connecting position, in which the closure element 52 and the socket wall 30 are in engagement in a force- and/or form-fitting manner, by screwing in about the longitudinal axis 50. FIG. 3 shows this connecting position schematically.

A wall thickness 82 of the predetermined breaking point 70 is preferably significantly smaller than the thickness 32 of the socket wall. In particular, the wall thickness 82 is less than 30% of the thickness 32. Depending on a thickness 32 of the socket wall 30, the wall thickness 82 may be even less than 10% of the thickness.

Figure 4:
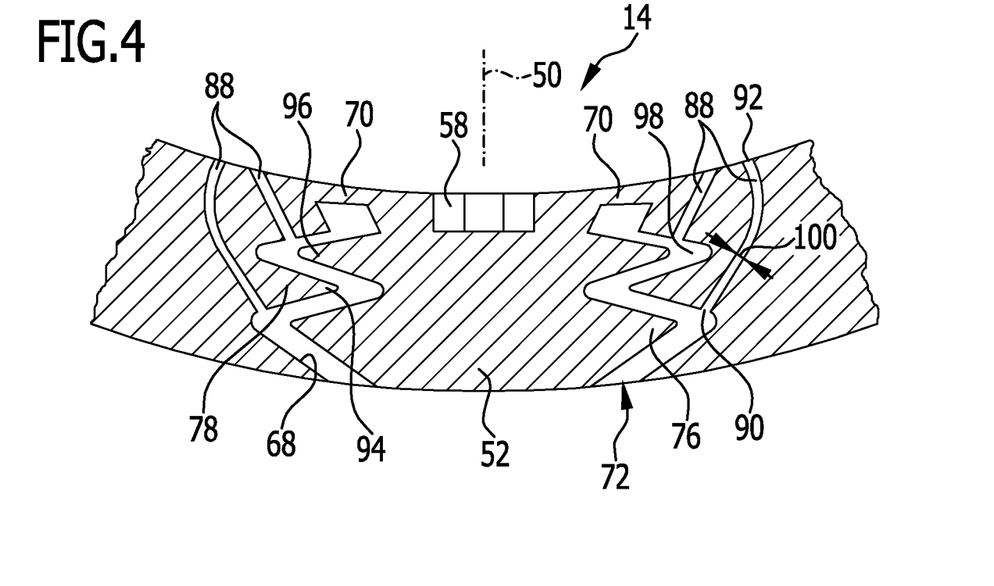
FIG. 4: shows a sectional view of a further embodiment of a joint socket in the region of a through-opening closed with a closure element.
Figure 5:
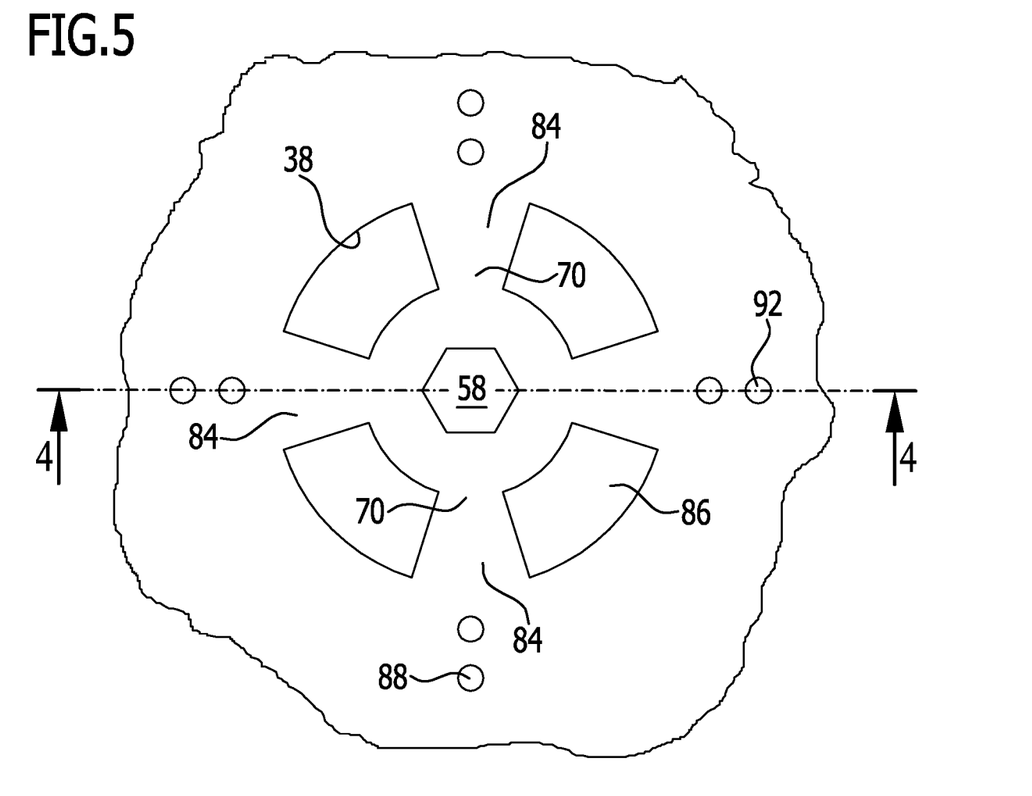
FIG. 5: shows a sectional view along line 4-4 in FIG. 4.

A further embodiment of a joint socket 14 is depicted in part in FIGS. 4 and 5. Here, too, the closure element 52 has, in turn, an external thread section 76 which, in cooperation with an internal thread section 78 which is formed on the rim 68 of the through-opening 38, forms a connecting device 72.

It can be seen in FIG. 5 that the external thread section 76 may comprise four segments which are separated from each other in circumferential direction and which are formed on projections 84 which project from the rim 68 in radial direction to the longitudinal axis 50. In total four projections 84 are formed which are distributed uniformly about the circumference of the rim 68 and extend over an angular range of about 30°. As a result, formed between two projections 84 is in each case one opening 86 which extends over a circumferential angle of about 60°.

In order to be able to produce the joint socket 14 in particular in a generative manufacturing process, one or more channels 88 may optionally be formed in the socket wall 30. These are drawn in for example in FIG. 4.

Each channel 88 passes through the socket wall 30 at least partially and has a first open end 90 and a second open end 92. The first open end 90 is arranged or formed in the region between the internal thread section 78, which forms a first connecting element 94 of the connecting device 72, and the external thread section 76, which forms a second connecting element 96 of the connecting device 72. The second open end 92 passes through the inner surface 36 of the socket wall 30. Alternatively, the second open end 92 may also pass through the outer surface 34 of the socket wall 30.

The channels 88 serve in particular for again removing pulverulent starting material, from which the socket joint 14 is formed, e.g., by selective laser melting or laser sintering, which is not solidified between the connecting elements 94 and 96, from a gap 98 formed between the connecting elements 94 and 96.

A diameter 100 of the channel 88 is at least about 5 times, preferably 10 times an average diameter of powder particles from which the joint socket is formed by a generative manufacturing process. It is preferably assured that the diameter 100 is in any case larger than a maximum diameter of the powder particles.

Also in the embodiment of the joint socket 14 depicted in FIGS. 4 and 5, the closure element 52 may be separated out of the socket wall 30 by destroying the predetermined breaking point 70. If the through-opening 38 is not required for the insertion of a fixing element, the latter may, as already described above, again be screwed into the through-opening 38 of the socket wall 30 by rotating in about the longitudinal axis 50, in order to enter into a force- and/or form-fitting connection therewith.

Figure 6:
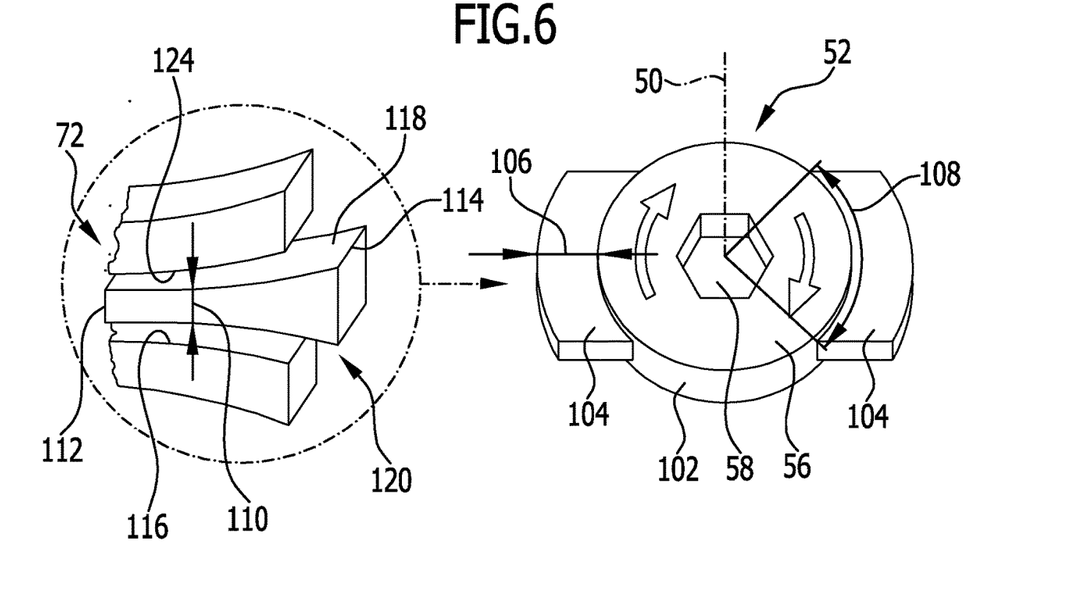
FIG. 6: shows a perspective schematic depiction of a further embodiment of a closure element with a partial section enlargement.
Figure 7:
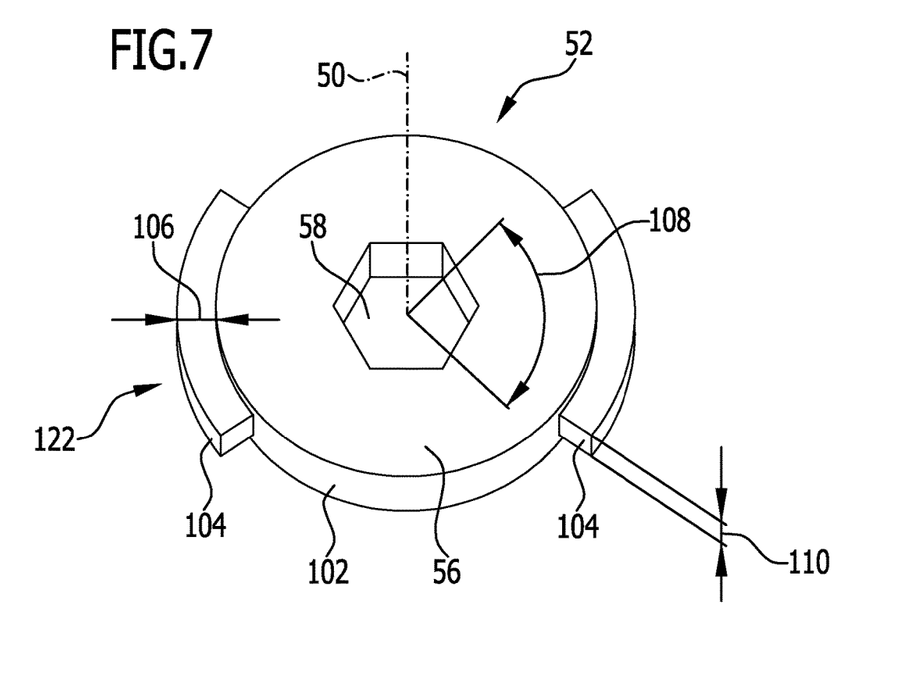
FIG. 7: shows a schematic perspective depiction of a further embodiment of a closure element.
Figure 8:
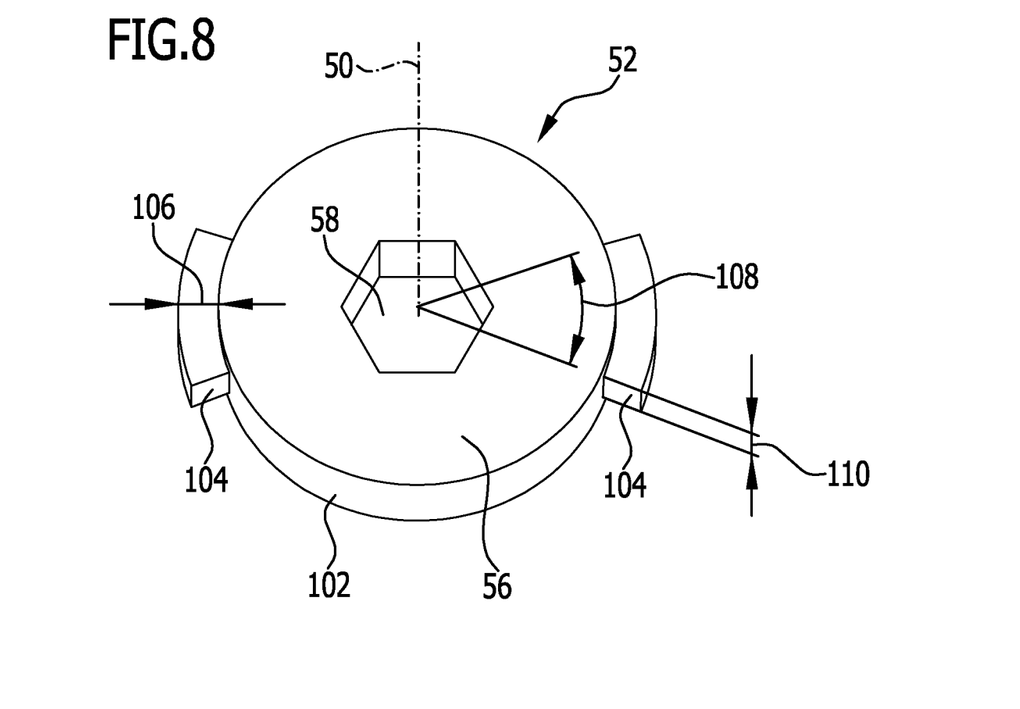
FIG. 8: shows a schematic depiction of a further embodiment of a closure element.

Further embodiments of closure elements 52 are depicted in FIGS. 6 to 8. They are likewise of substantially discoidal configuration and have a tool element receptacle 58 facing away from the inner surface 56 thereof.

Two protruding projections 104 are formed facing away from each other in diametrical direction on a circumferential rim 102 peripherally surrounding the closure element 52. These differ from each other in the various embodiments substantially in a height 106 in radial direction commencing from the longitudinal axis 50, as well as a circumferential angle 108 over which the projection 104 extends in circumferential direction in relation to the longitudinal axis 20.

Further, a thickness 110 of the projections 104 in parallel to the longitudinal axis 50 may change depending on the circumferential angle 108. In the sectional view in FIG. 6, it is schematically depicted how this thickness 110 continuously increases in circumferential direction commencing from a first end 112 to a second end 114. Thus by rotating the closure element 50 about the longitudinal axis when the projection 104 projects into a corresponding recess 116, not depicted in FIGS. 6 to 8, which is formed in the region of the rim 68 of the joint socket 14, the closure element 52 may be clamped to the socket wall 30. This may be achieved in particular if inner surfaces of the recess 116 which face each other slide on side faces 118 of the projection 104 which face away from each other, until a rotation is no longer possible. Thus, a connecting device 72 may selectively be configured in the form of a turning clamp connecting device 120 or, if a thickness 110 remains constant irrespective of the circumferential angle 108, a bayonet connecting device 122.

The recess 116 corresponding to the projection 104 is formed in the rim 68 open facing in the direction toward the longitudinal axis 50. Conversely, the recess 116 may also be formed on the closure element 52 and be arranged or formed open facing away in radial direction in relation to the longitudinal axis 50. A corresponding projection 104 is then formed protruding from the rim 68.

The recess 116 may in particular be configured in the form of a groove 124 running in circumferential direction in relation to the longitudinal axis 50.

In addition, the recess 116 may be open at least in sections facing in the direction toward the center 48 of the shell 28 for forming an insertion opening for the projection 104 or at least a part thereof in an insertion direction running parallel or substantially parallel to the longitudinal axis 50.

In particular, when the predetermined breaking point 70 is undamaged, the projection 104 may be arranged in a neutral position of the at least one connecting device 72 in which the projection 104 is arranged in the insertion opening or in the region of the insertion opening of the recess 116.

This enables in particular that the closure element 52 in a neutral position even with the predetermined breaking point 70 irreversibly broken is neither in engagement in a force- nor a form-fitting manner with the socket wall 30.

Figure 9:
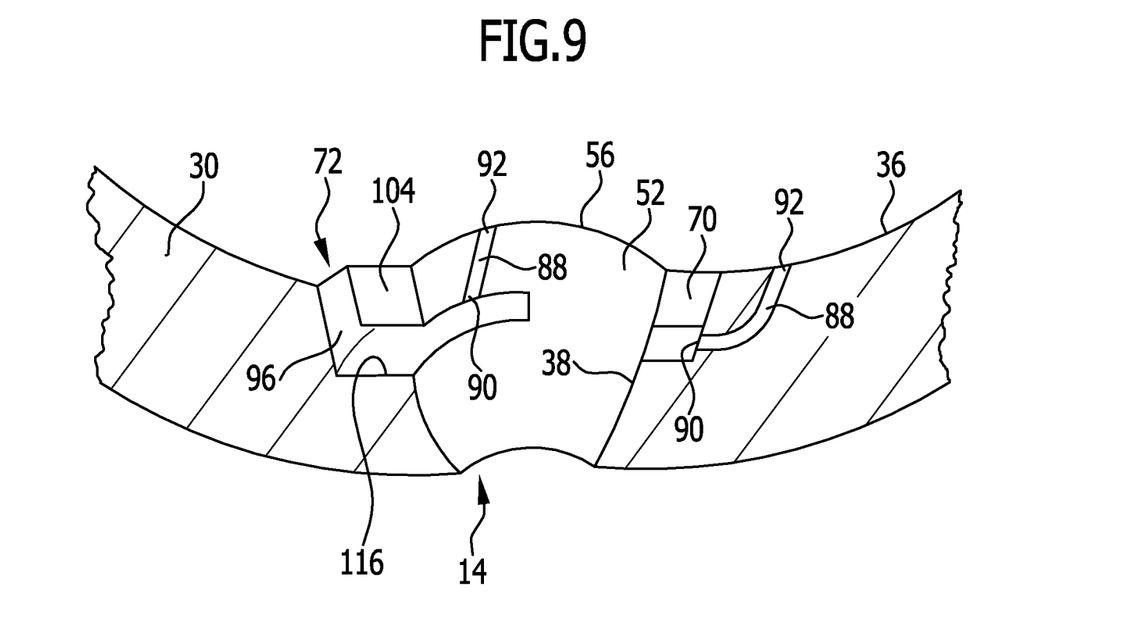
FIG. 9: shows a sectional view similar to FIG. 3 of a further embodiment of a joint socket in the region of a through-opening closed with a closure element.

A further embodiment of a joint socket 14 is schematically depicted in FIG. 9. In the said embodiment, the closure element 52, in turn, is connected to the socket wall 30 as one piece by way of a predetermined breaking point.

Channels 88 are formed both on the socket wall 30 and on the closure element 52 and open with their second end 92 at the inner surface 36 and the inner surface 56, respectively.

First ends 90 of the channels 88, however, open into a region between the recess 116 forming a first connecting element 94 and the projection 104 forming a second connecting element 96 of the connecting device 72. Here, the connecting device 72 is arranged in a neutral position with the predetermined breaking point 70 not destroyed. From this position, the closure element 52 may fall unhindered out of the through-opening 38 when the predetermined breaking point 70 or the multiple predetermined breaking points 70, respectively, are irreversibly destroyed.

By appropriately rotating the closure element 52 in the through-opening 38 about the longitudinal axis 50, a clamping between the projections 104 on the closure element 52 and corresponding recesses 116 on the rim 68 of the joint socket 30 may arise. In the connecting position thus defined, the closure element 52 is arranged in the through-opening 38 in a force- and optionally also form-fitting manner so as to close the same.

As already mentioned, the joint socket 14 is preferably formed as one piece. In particular, it is formed monolithically, i.e., from one piece.

It may be produced, e.g., by a generative manufacturing process. For example, it may hereby be concerning a powder bed process, a free-forming process, or a liquid material process. Other layer structure processes are also conceivable for forming the joint socket 14.

As described at the outset, apart from selective laser melting or laser sintering, selective heat sintering may also be used. The joint socket 14 may also be formed by solidifying powder material by means of a binder or by electron beam melting of a pulverulent starting material. Deposition welding or metal powder deposition processes are suitable for forming the described joint socket 14.

The joint socket 14 may in particular be made of a metal and/or of a plastic. The metal preferably is titanium or contains titanium. The plastic may in particular be or contain polyetheretherketone.

REFERENCE NUMERAL LIST

10 joint endoprosthesis
12 hip joint endoprosthesis
14 joint socket
16 hip joint socket
18 shank
20 femur shank
22 joint head
24 joint insert
26 joint head receptacle
28 shell
30 socket wall
32 thickness
34 outer surface
36 inner surface
38 through-opening
40 apex region
42 opening
44 circle
46 rotational axis
48 center
50 longitudinal axis
52 closure element
54 outer surface
56 inner surface
58 tool element receptacle
60 hexagonal socket
62 rim
64 numbering
66 web
68 rim
70 predetermined breaking point
72 connecting device
74 screw connecting device
76 external thread section
78 internal thread section
80 fixing element
82 wall thickness
84 projection
86 opening
88 channel
90 first end 92 second end
94 first connecting element
96 second connecting element
98 gap
100 diameter
102 circumferential edge
104 projection
106 height
108 circumferential angle
110 thickness
112 first end
114 second end
116 cutout
118 sides
120 pressure clamp device
122 bayonet connecting device
124 groove

What is claimed is:

1. A joint socket for a joint endoprosthesis, the joint socket having the form or substantially the form of a section of a hollow-spherical shell, the joint socket comprising:
a socket wall,
at least one through-opening formed in the socket wall, the through-opening being closed with a closure element, the closure element being formed as one piece with the socket wall, and
at least one connecting device,
wherein:
at least one predetermined breaking point is formed between the closure element and the socket wall,
the at least one predetermined breaking point is irreversibly destroyable for removing the closure element from the socket wall,
the at least one connecting device at least one of force-fittingly and form-fittingly connects the closure element removed from the socket wall to the socket wall in a connecting position,
the at least one connecting device is configured in the form of one of a screw connecting device, a bayonet connecting device, a turning clamp connecting device, or a snapping connecting device.

2. The joint socket in accordance with claim 1, wherein the joint socket has a spherical or substantially spherical outer surface and a hollow-spherical or substantially hollow-spherical inner surface.

3. The joint socket in accordance with claim 1, wherein:
the at least one connecting device comprises at least one first connecting element and at least one second connecting element,
the at least one first connecting element is arranged or formed on the socket wall, and
the at least one second connecting element is arranged or formed on the at least one closure element.

4. The joint socket in accordance with claim 3, wherein at least one of:
a) the at least one first connecting element and the at least one second connecting element in the connecting position are in engagement in at least one of a force-fitting and form-fitting manner and in a separating position, in which the at least one predetermined breaking point is irreversibly destroyed and the closure element unblocks the at least one through-opening, are disengaged;
b) the at least one first or second connecting element comprises an internal or external thread section; and
c) the at least one first or second connecting element is configured in the form of a projection or in the form of a recess corresponding to the projection.

5. The joint socket in accordance with claim 1, wherein the at least one through-opening defines a longitudinal axis which runs in a radial direction or substantially in a radial direction in relation to a center of the shell.

6. The joint socket in accordance with claim 5, wherein:
the at least one connecting device comprises at least one first connecting element and at least one second connecting element,
the at least one first or second connecting element comprises an internal or external thread section,
the at least one first or second connecting element is configured in the form of a projection, and
the internal or external thread section is arranged or formed on the projection.

7. The joint socket in accordance with claim 6, wherein:
the recess is open at least in sections facing in a direction toward a center of the shell for forming an insertion opening for the projection,
when the predetermined breaking point is undamaged, the projection is arranged in a neutral position of the at least one connecting device in which the projection is arranged in the insertion opening or in the region of the insertion opening.

8. The joint socket in accordance with claim 7, wherein the closure element in the neutral position of the at least one connecting device with the predetermined breaking point irreversibly destroyed is neither in engagement in a force- nor a form-fitting manner with the socket wall.

9. The joint socket in accordance with claim 4, wherein at least one of:
a) the at least one first or second connecting element is configured in the form of a projection, wherein the projection is arranged or formed protruding from the at least one closure element in the radial direction in relation to the longitudinal axis or projecting from a rim of the socket wall delimiting the through-opening in a direction toward the longitudinal axis;
b) the at least one first or second connecting element is configured in the form of a recess corresponding to the projection, wherein the recess corresponding to the projection is arranged or formed in a rim of the socket wall, the rim delimiting the through-opening, so as to be open facing in a direction toward the longitudinal axis or open facing from the at least one closure element in the radial direction in relation to the longitudinal axis;
c) the at least one first or second connecting element is configured in the form of a recess, wherein the recess comprises at least one groove section open facing in a direction toward the longitudinal axis or in the radial direction away from the longitudinal axis; and
d) the at least one first or second connecting element is configured in the form of a projection, wherein the at least one second connecting element is configured in the form of a recess corresponding to the projection and wherein the recess is open at least in sections facing in a direction toward a center of the shell for forming an insertion opening for the projection or at least a part thereof in an insertion direction running parallel or substantially parallel to the longitudinal axis.

10. The joint socket in accordance with claim 3, wherein in the socket wall is formed at least one powder channel which at least partially passes through the socket wall and has a first open end and a second open end, and wherein the first open end is arranged or formed in the region of the first or second connecting element, and wherein the second open end passes through the outer surface or the inner surface of the socket wall.

11. The joint socket in accordance with claim 10, wherein at least one of:
a) a diameter of the at least one powder channel corresponds to at least about 5 times the average diameter of powder particles from which the joint socket is formed by a generative manufacturing process, and
b) the joint socket comprises a multitude of powder channels.

12. The joint socket in accordance with claim 1, wherein the at least one predetermined breaking point has a wall thickness which is significantly smaller than a thickness of the socket wall.

13. The joint socket in accordance with claim 12, wherein the wall thickness of the breaking point is less than 0.2 times the thickness of the socket wall.

14. The joint socket in accordance with claim 1, wherein at least one of:
a) the at least one first connecting element and the at least one second connecting element in the connecting position are in engagement in at least one of a force-fitting and form-fitting manner and in a separating position, in which the at least one predetermined breaking point is irreversibly destroyed and the closure element unblocks the at least one through-opening, are disengaged, the at least one closure element which is separated out of the socket wall by destroying the at least one predetermined breaking point is transferable from the separating position into the connecting position by screwing in about a longitudinal axis defined by the through-opening or a rotating-in movement about the longitudinal axis,
b) the at least one closure element comprises at least one tool element receptacle, and
c) the at least one closure element comprises at least one tool element receptacle and wherein the at least one tool element receptacle is open facing in a direction toward the center of the shell, and
d) the joint socket is formed monolithically.

15. The joint socket in accordance with claim 1, wherein the joint socket is formed by a generative manufacturing process.

16. The joint socket in accordance with claim 15, wherein the joint socket is formed by at least one of:
a) a powder bed process, a free-forming process, a liquid material process, or a different layering process; and
b) selective laser melting, selective laser sintering, selective heat sintering, solidifying powder material by means of binder, electron beam melting, deposit welding, a metal powder deposition process, cold gas spraying, stereolithography, a process using digital light processing for illumination, lamination by sheets, 3D screen printing of metals, or light-controlled electrophoretic deposition.

17. The joint socket in accordance with claim 1, wherein the joint socket is made of at least one of a metal and of a plastic.

18. The joint socket in accordance with claim 17, wherein at least one of:
a) the metal is or contains titanium; and
b) the plastic is or contains polyetheretherketone.

19. The joint socket in accordance with claim 1, wherein:
the at least one closure element comprises at least one tool element receptacle; and
the at least one tool element receptacle is configured in the form of a recess or in the form of a projection.

20. The joint socket in accordance with claim 19, wherein the at least one tool element receptacle is configured in the form of the recess with one of a polygonal cross section or an internal multi-round.

21. The joint socket in accordance with claim 1, wherein:
the at least one closure element comprises at least one tool element receptacle; and
the at least one tool element receptacle is open facing in a direction toward a center of the shell.

22. The joint socket in accordance with claim 1, wherein the at least one predetermined breaking point comprises a plurality of webs running in radial direction in relation to a longitudinal axis of the at least one through-opening, the webs connecting the closure element to a rim of the at least one through-opening.

23. A joint endoprosthesis, comprising:
a joint socket and a shank, the shank being coupled to the joint socket in a ball-jointed manner, wherein the joint socket is configured in the form of a joint socket having the form or substantially the form of a section of a hollow-spherical shell, the joint socket comprising:
a socket wall,
at least one through-opening formed in the socket wall, the through-opening being closed with a closure element, the closure element being formed as one piece with the socket wall, and
at least one connecting device,
wherein:
at least one predetermined breaking point is formed between the closure element and the socket wall,
the at least one predetermined breaking point is irreversibly destroyable for removing the closure element from the socket wall,
the at least one connecting device at least one of force-fittingly and form-fittingly connects the closure element removed from the socket wall to the socket wall in a connecting position,
the at least one connecting device is configured in the form of one of a screw connecting device, a bayonet connecting device, a turning clamp connecting device, or a snapping connecting device.

24. The joint endoprosthesis in accordance with claim 23, wherein the shank comprises a ball-shaped or substantially ball-shaped joint head, and wherein the joint socket comprises a joint insert with a joint head receptacle corresponding to the joint head.

25. The joint socket in accordance with claim 23, wherein:
the at least one closure element comprises at least one tool element receptacle; and
the at least one tool element receptacle is open facing in a direction toward a center of the shell.

26. The joint socket in accordance with claim 23, wherein the at least one predetermined breaking point comprises a plurality of webs running in radial direction in relation to a longitudinal axis of the at least one through-opening, the webs connecting the closure element to a rim of the at least one through-opening.

27. A joint socket for a joint endoprosthesis, the joint socket having the form or substantially the form of a section of a hollow-spherical shell, the joint socket comprising:
a socket wall,
at least one through-opening formed in the socket wall, the through-opening being closed with a closure element, the closure element being formed as one piece with the socket wall, and at least one connecting device,
wherein:
at least one predetermined breaking point is formed between the closure element and the socket wall,
the at least one predetermined breaking point is irreversibly destroyable for removing the closure element from the socket wall,
the at least one connecting device at least one of force-fittingly and form-fittingly connects the closure element removed from the socket wall to the socket wall in a connecting position,
the at least one connecting device comprises at least one first connecting element and at least one second connecting element,
the at least one first connecting element is arranged or formed on the socket wall,
the at least one second connecting element is arranged or formed on the at least one closure element,
the at least one first connecting element comprises an internal thread section, and
the at least one second connecting element comprises an external thread section, and
the external thread section corresponds to the internal thread section.

28. The joint socket in accordance with claim 27, wherein the at least one predetermined breaking point comprises a plurality of webs running in radial direction in relation to a longitudinal axis of the at least one through-opening, the webs connecting the closure element to a rim of the at least one through-opening.

* * * * *